US012544273B2

(12) United States Patent
Holm et al.

(10) Patent No.: US 12,544,273 B2
(45) Date of Patent: Feb. 10, 2026

(54) WOUND DRESSING

(71) Applicant: Solventum Intellectual Properties Company, Maplewood, MN (US)

(72) Inventors: David R. Holm, Hudson, WI (US); Richard L. Jacobson, Stillwater, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 395 days.

(21) Appl. No.: 17/766,571

(22) PCT Filed: Oct. 6, 2020

(86) PCT No.: PCT/IB2020/059383

§ 371 (c)(1),
(2) Date: Apr. 5, 2022

(87) PCT Pub. No.: WO2021/070058

PCT Pub. Date: Apr. 15, 2021

(65) Prior Publication Data

US 2024/0099896 A1 Mar. 28, 2024

Related U.S. Application Data

(60) Provisional application No. 62/911,760, filed on Oct. 7, 2019.

(51) Int. Cl.

| | |
|---|---|
| ***A61F 13/0203*** | (2024.01) |
| ***A61F 13/00*** | (2024.01) |
| ***A61F 13/02*** | (2024.01) |

(52) U.S. Cl.
CPC .... *A61F 13/0226* (2013.01); *A61F 13/00063* (2013.01)

(58) Field of Classification Search
CPC .. A61F 2013/00148; A61F 2013/00285; A61F 2013/00523; A61F 2013/0054; A61F 2013/00544; A61F 2013/00604; A61F 2013/00608; A61F 2013/00676; A61F 13/00063; A61F 13/024; A61F 13/0226; A61F 13/0236; A61F 13/0259; A61F 13/023; A61F 13/0246; A61F 13/0253; A61F 13/60; A61F 2013/00259; A61F 2013/00582; A61L 15/44; A61K 9/70
See application file for complete search history.

(56) References Cited

U.S. PATENT DOCUMENTS

| | | | |
|---|---|---|---|
| 5,147,338 | A | 9/1992 | Lang |
| 5,531,855 | A | 7/1996 | Heinecke |
| 6,169,224 | B1 | 1/2001 | Heinecke |
| 6,436,432 | B2 | 8/2002 | Heinecke |

(Continued)

FOREIGN PATENT DOCUMENTS

| | | |
|---|---|---|
| WO | WO 1992-005756 | 4/1992 |
| WO | WO 2015-102981 | 7/2015 |

(Continued)

OTHER PUBLICATIONS

International Search Report for PCT International Application No. PCT/IB2020/059383, mailed on Feb. 10, 2021, 4 pages.

*Primary Examiner* — Alireza Nia
*Assistant Examiner* — Andrew Jun-Wai Mok

(57) ABSTRACT

Wound dressings having a delivery system are provided.

20 Claims, 12 Drawing Sheets

(56) References Cited

U.S. PATENT DOCUMENTS

| | | | | |
|---|---|---|---|---|
| 6,838,589 | B2 | 1/2005 | Liedtke | |
| 2014/0188090 | A1 | 7/2014 | Riesinger | |
| 2016/0317358 | A1 * | 11/2016 | Holm | A61F 13/024 |
| 2019/0231604 | A1 | 8/2019 | Holm | |

FOREIGN PATENT DOCUMENTS

| | | | | |
|---|---|---|---|---|
| WO | WO 2018-067758 | | 4/2018 | |
| WO | WO-2018067758 | A1 * | 4/2018 | A61F 13/064 |

* cited by examiner

WOUND DRESSING

CROSS REFERENCE TO RELATED APPLICATIONS

This application is a national stage filing under 35 U.S.C. 371 of PCTIB2020/059383, filed Oct. 6, 2020, which claims the benefit of Provisional Application No. 62/911,760, filed Oct. 7, 2019, the disclosures of each of which are incorporated by reference herein in their entireties.

BACKGROUND

Many different types of skin traumas benefit from preventing infection and promoting healing. Such traumas are often cared for with dressings that protect the area from microorganisms, dirt and debris, and further trauma. In some instances, dressings may allow for delivery and/or localizing of therapeutics. However, not all skin traumas are easy to effectively dress or cover. For example, long injuries such as surgical incisions can be difficult to cover because they are not always linear, or they often require the use of multiple dressings partly because dressings of greater size are not easily handled or available. The use of multiple dressings requires cutting and customizing of the dressings which is time consuming and can result in difficult application of the dressing which can result in poor coverage and sealing of the injury from contaminants. Likewise, nonlinear traumas can require the use of multiple dressings because the dressing is not able to flex or bend adequately during application. In addition, traumas that traverse nonplanar surfaces, e.g., long and/or nonlinear traumas over bendable surfaces, suffer from the lack of adequate dressing conformability coupled with adequate support to handling during application to the nonplanar surface of the body.

Despite the advances in wound dressing systems, there remains a need for wound dressings that are conformable, resilient, and easy to use for long and relatively narrow types of skin traumas.

SUMMARY

In one embodiment, a wound dressing is described. The wound dressing may include an elongated composite and a delivery system. The elongated composite may include a flexible substrate. The elongated composite may include a first surface and a second surface opposite the first surface, a perimeter comprising a first end, a second end opposite the first end, a first edge and a second edge opposite the first edge, a length defined by a distance between the first end and the second end, and a width defined by a distance between the first edge and the second edge. The delivery system may include a first support network, a second support network, and a third support network, each releasably attached to the second surface. The first support network may include a first hub medially nested along the width, and at least one phalange extending from the first hub to the perimeter. The second support network may include a second hub medially nested along the width, and at least one phalange extending from the second hub to the perimeter. The third support network may include a third hub medially nested along the width, and at least one phalange extending from the third hub to the perimeter. The third support network may separate the first support network from the second support network. The first, second, and third support network may be separated from one another to expose the second surface of the elongated composite.

In another embodiment, a wound dressing is described. The wound dressing may include an elongated composite and a delivery system. The elongated composite may include a first surface and a second surface opposite the first surface, a perimeter comprising a first end, a second end opposite the first end, a first edge and a second edge opposite the first edge, a length defined by a distance between the first end and the second end, and a width defined by a distance between the first edge and the second edge. The elongated composite may include a flexible substrate adjacent the second surface and extending to the perimeter, and a therapeutic layer adjacent the first surface. The therapeutic layer may be removed from the perimeter. The delivery system may include a first support network and a second support network, each network releasable attached to the second surface. The first support network may include a first hub and a phalange extending from the first hub beyond the perimeter at the first edge to form a handling tab. The second support network may include a second hub and a phalange extending from the second hub beyond the perimeter at the second edge to form a handling tab. A straight line passing from one or more handling tab to the opposite edge, traverses the therapeutic layer.

BRIEF DESCRIPTION OF DRAWINGS

FIG. 1A.

FIG. 1A.

DETAILED DESCRIPTION

The disclosed wound dressing(s) include an elongated composite and a delivery system with at least three disconnected support networks that allow for enhanced handling of the dressing and flexibility in placement over wounds, especially long and narrow wounds or non-linear wounds.

The following figure descriptions provide numerical identifiers for the features described. The second and third significant figure in each numerical identifier is conserved with respect to figure feature. For example, a first support network in FIG. 1 is 120, in FIG. 2 is 220, in FIG. 3 is 320, and so forth. It is to be understood that not all features are identified numerically in each figure in order to promote visual clarity.

Figure 1A:
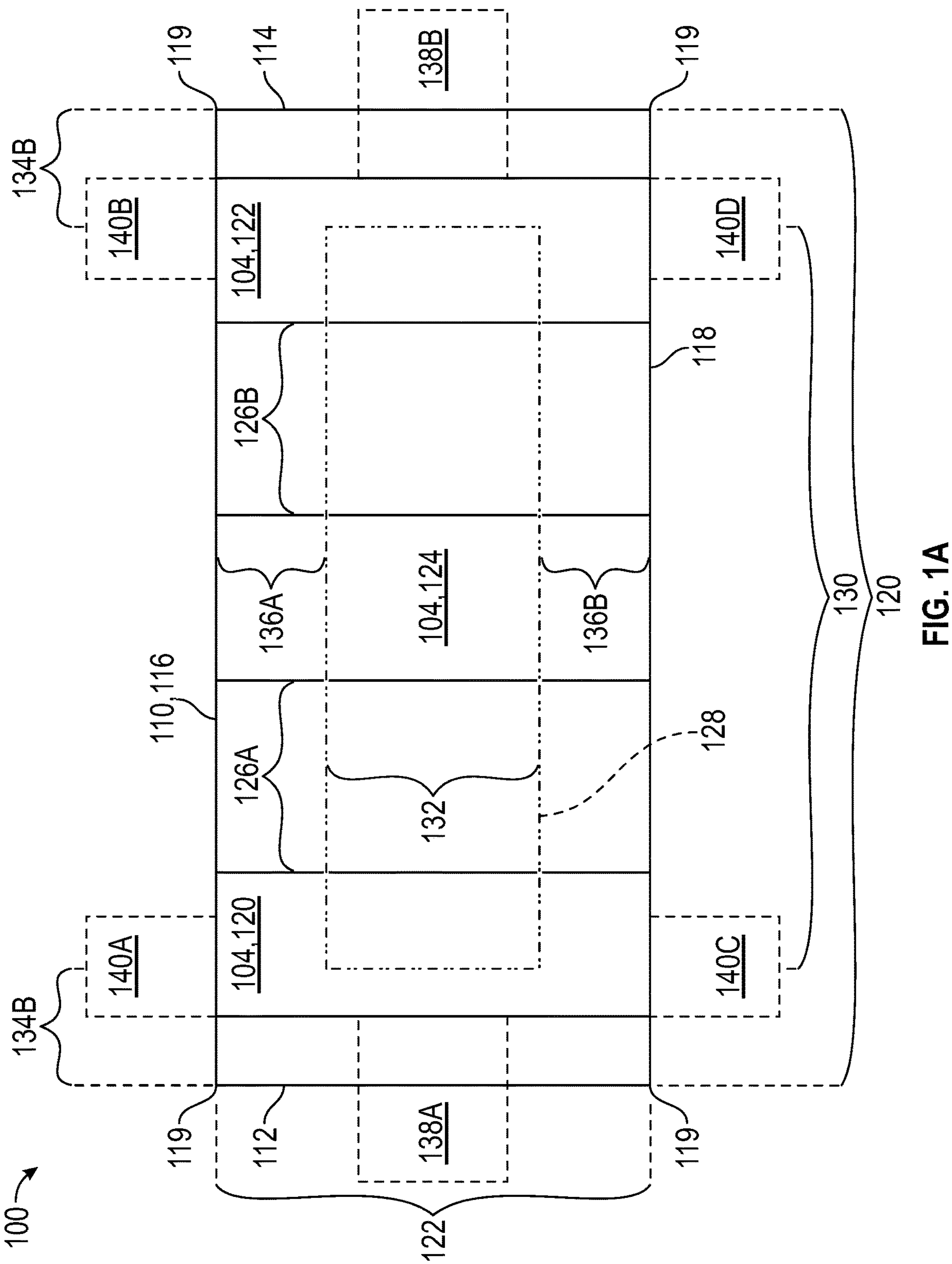
FIG. 1A is a schematic top plan view of a wound dressing of the present disclosure
Figure 2:
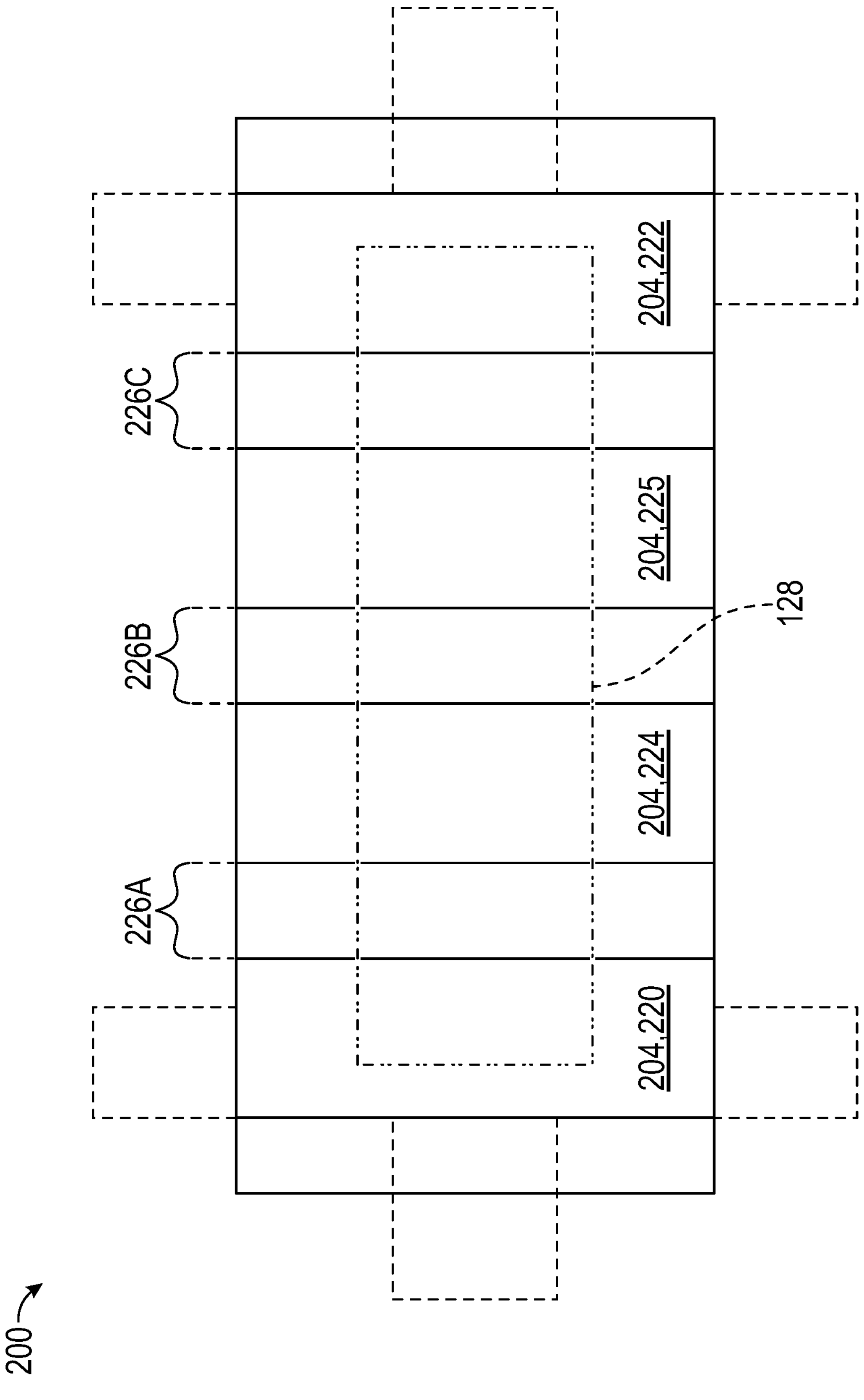
FIG. 2 is a schematic top plan view of a wound dressing of the present disclosure.
Figure 3:
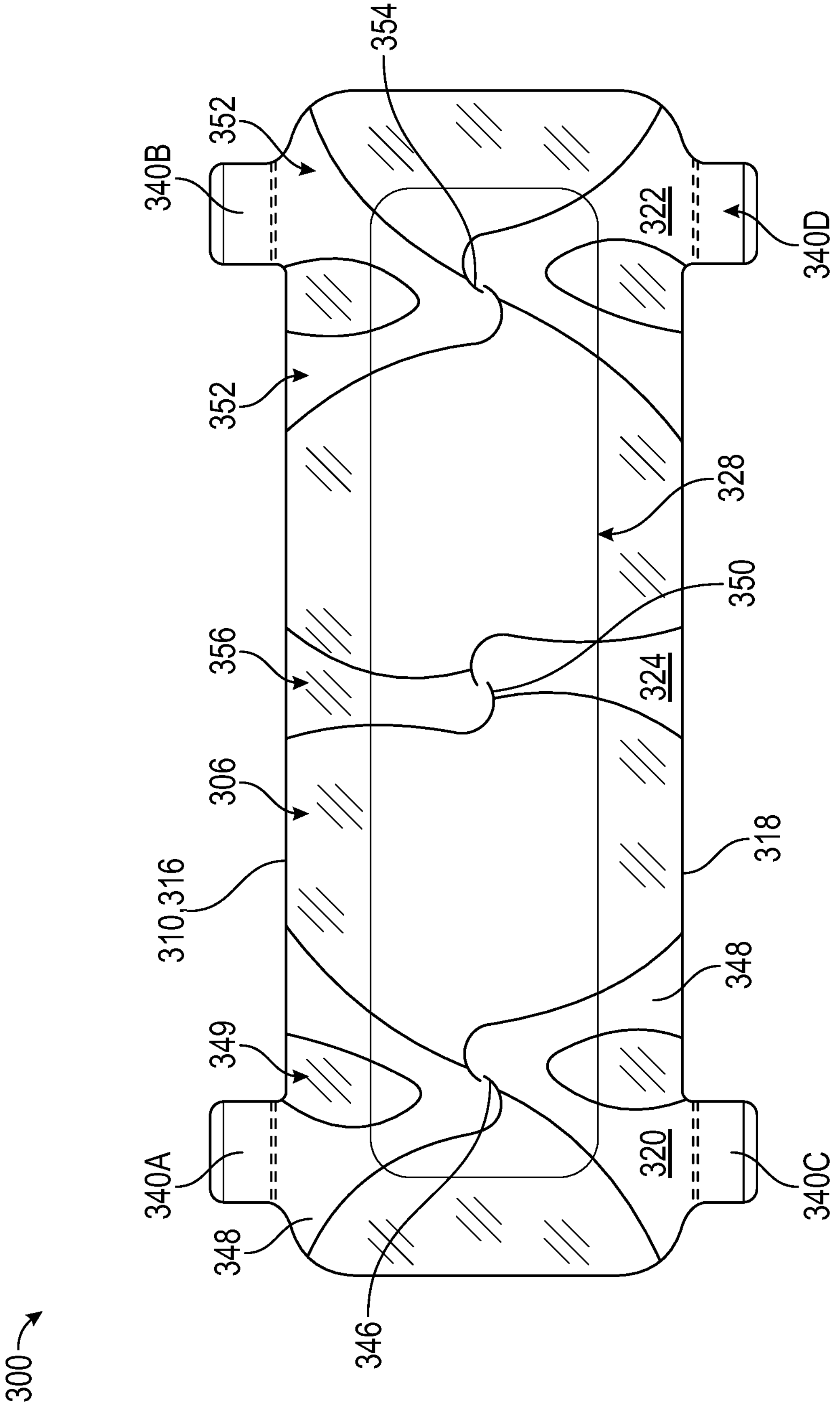
FIG. 3 is a schematic top plan view of one embodiment of a wound dressing.

FIG. 1A and FIG. 2 generally relate to wound dressings of the present disclosure. FIGS. 3-8 describe example wound dressings of the present disclosure. It is to be understood that any features of one embodiment, unless indicated otherwise, may be included or combined with features of other embodiments described herein.

FIG. 1A illustrates a wound dressing 100. Wound dressing 100 includes an elongated composite (not shown, see 102 in FIGS. 1B and 1C) and a delivery system 104. Elongated composite (102) includes a flexible substrate (not shown, see 106 in FIGS. 1B and 1C) and a perimeter 110. The flexible substrate includes a first surface (not shown, see 107 in FIGS. 1B and 1C) and a second surface (not shown, see 108 in FIGS. 1B and 1C) opposite the first surface. Perimeter 110 defines a first end 112, a second end 114, a first edge 116, a second edge 118, and four corners 119. Elongated composite (102) includes a length 120 and a width 122. Length 120 is defined by the distance between first end 112 and second end 114. Width 122 is defined by the distance between first edge 116 and second edge 118. Delivery system 104 includes a first support network 120, a second support network 122, and a third support network 124 releasably attached to second surface (108). Third support network 124 separates first support network 120 from second support network 122 which exposes exposed surfaces 126A and 126B of elongated composite (102). The exposed surfaces 126A and 126B are highly flexible and stretchy portions of the elongated composite.

In some embodiments, wound dressing 100 includes a therapeutic layer 128 having a therapeutic length 130 and a therapeutic width 132. As shown, the perimeter of the therapeutic layer is removed from, i.e., less than, perimeter 110. Therapeutic layer 128 may be separated from perimeter 110 by end distances 134A and 134B, and by edge distances 136A and 136B. A user of wound dressing 100 may cut elongated composite (102) along width 112 in order to remove one or more end distances 134A and 134B to provide a wound dressing capable of being applied end-long with another wound dressing without interrupting the wound-coverage area of therapeutic layer 128. Cutting the end distances from the dressing results in a both a modified dressing and an end distance cut portion that have handling tabs on opposite edges of the cut for both pieces which enables handling of these two pieces to further cover and seal the trauma site.

In some embodiments, wound dressing 100 includes one or more end handling tabs 138A and 138B, one or more edge handling tabs 140A. 140B. 140C, and 140D, or any combination thereof.

Figure 1B:
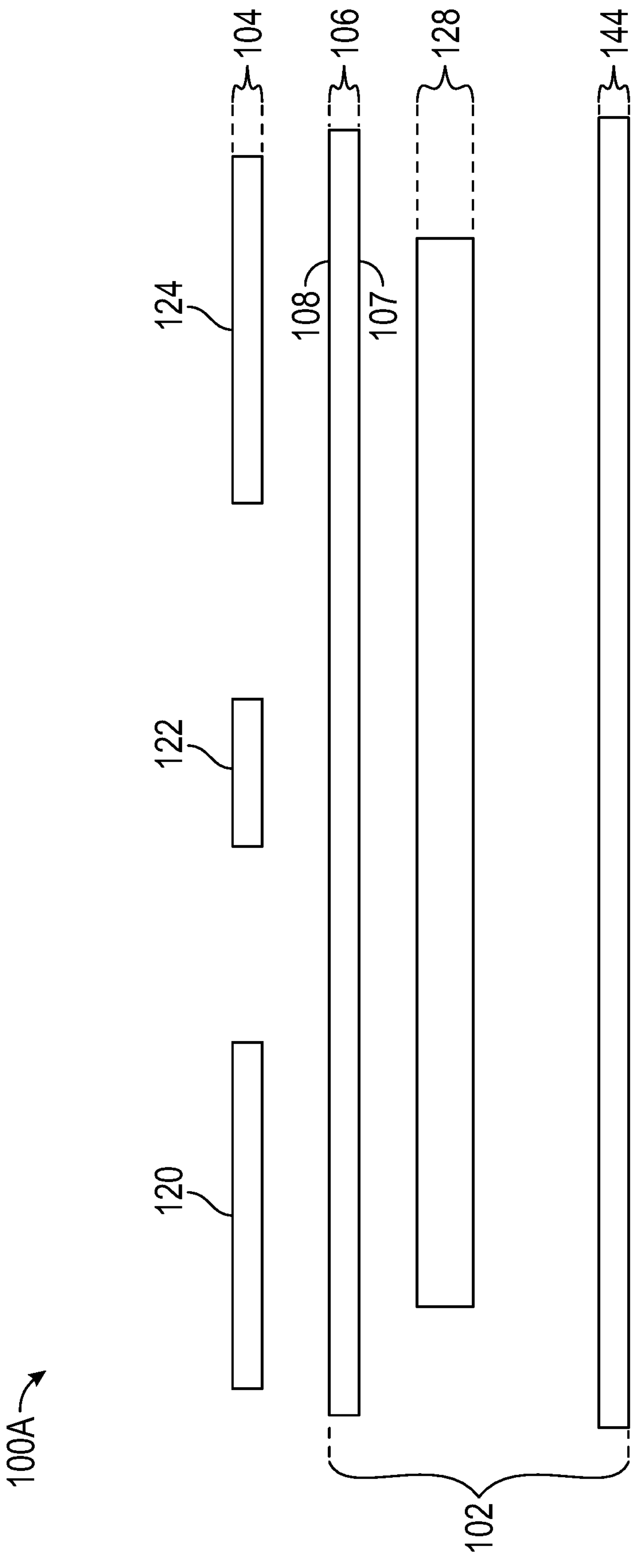
FIG. 1B is a schematic cross-sectional view of the wound dressing in, for example.

FIG. 1B illustrates a cross-sectional view of wound dressing 100 including elongated composite 102 and delivery system 104. Elongated composite 102 includes flexible substrate 106 having first surface 107 and second surface 108, therapeutic layer 128, and release liner 144.

Figure 1C:
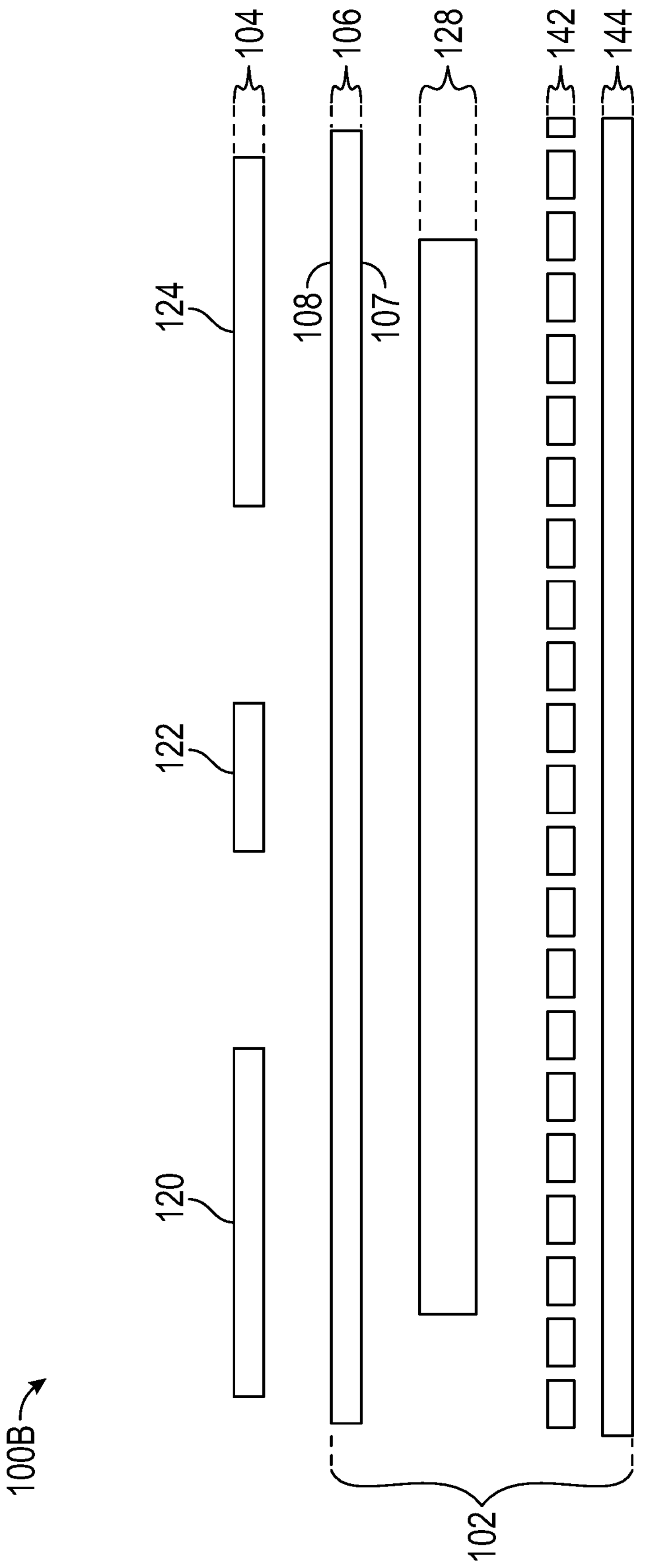
FIG. 1C is a schematic cross-sectional view of the wound dressing in, for example.

FIG. 1C illustrates a cross-sectional view of wound dressing 100 including elongated composite 102, delivery system 104, flexible substrate 106 having first surface 107 and second surface 108, and therapeutic layer 128. Wound dressing 100 may further include a perforated layer 142 and a release liner 144.

FIG. 2 illustrates a wound dressing 200. Wound dressing 200 includes all numbered the features of wound dressing 100, including those numbered accordingly. Some numbers are omitted for clarity. Wound dressing 200 includes a delivery system 204 that includes a first support network 220, a second support network 222, a third support network 224, and a fourth support network 225 releasably attached to the second surface of the flexible substrate (not shown). Third support network 224 and fourth support network 225 separate first support network 220 from second support network 222 which exposes exposed surfaces 226A, 226B, and 227C of the second surface. Cross-sectional views (not shown) of wound dressing 200 are similar to those shown in FIGS. 1A and 1B.

FIG. 3 illustrates a wound dressing 300. Wound dressing 300 includes all numbered features of wound dressing 100, including those numbered accordingly. Wound dressing 300 further illustrates first support network 320 including a first hub 346. First hub 346 includes phalange(s) 348 extending from first hub 346 to perimeter 310. As shown, phalange(s) 348 extend to first edge 316 and second edge 318. Exposed phalange surfaces 349 separate phalanges 348 exposing the second surface of the flexible substrate 306. Second support network 322 includes a second hub 350. Second hub 350 includes phalange(s) 352 extending from second hub 350 to perimeter 310. As shown, phalange(s) 352 extend to first edge 316 and second edge 318 (approaching corners). Third support network 324 includes a third hub 354. Third hub 354 includes phalange(s) 356 extending from third hub 354 to perimeter 310. As shown, a portion of the support networks overlap with therapeutic layer 328. Wound dressing 300 further includes edge handling tabs 340A. 340B. 340C, and 340D formed from phalanges 348 and 352.

Figure 4:
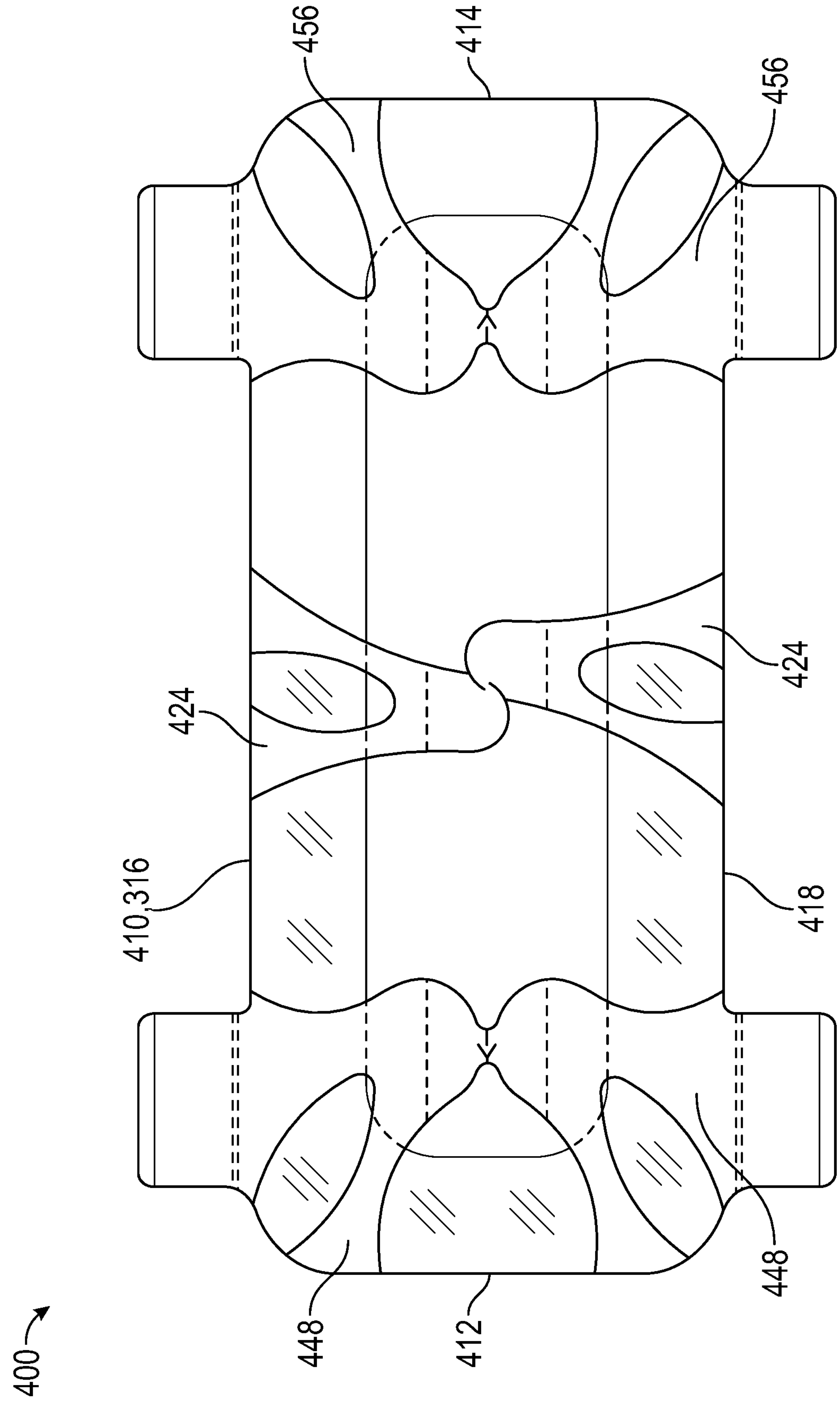
FIG. 4 is a schematic top plan view of one embodiment of a wound dressing.

FIG. 4 illustrates a wound dressing 400. Wound dressing 400 includes all numbered features of wound dressing 100 and 300, including those numbered accordingly. Wound dressing 400 differs from that of wound dressing 300, at least in part, in that the phalange(s) 448 and 456 extend to perimeter 410 at first edge 416, second edge 418, first end 412, and second end 414. Wound dressing 400 further includes additional third support network 424 phalange(s) 456 as compared to wound dressing 300.

Figure 5:
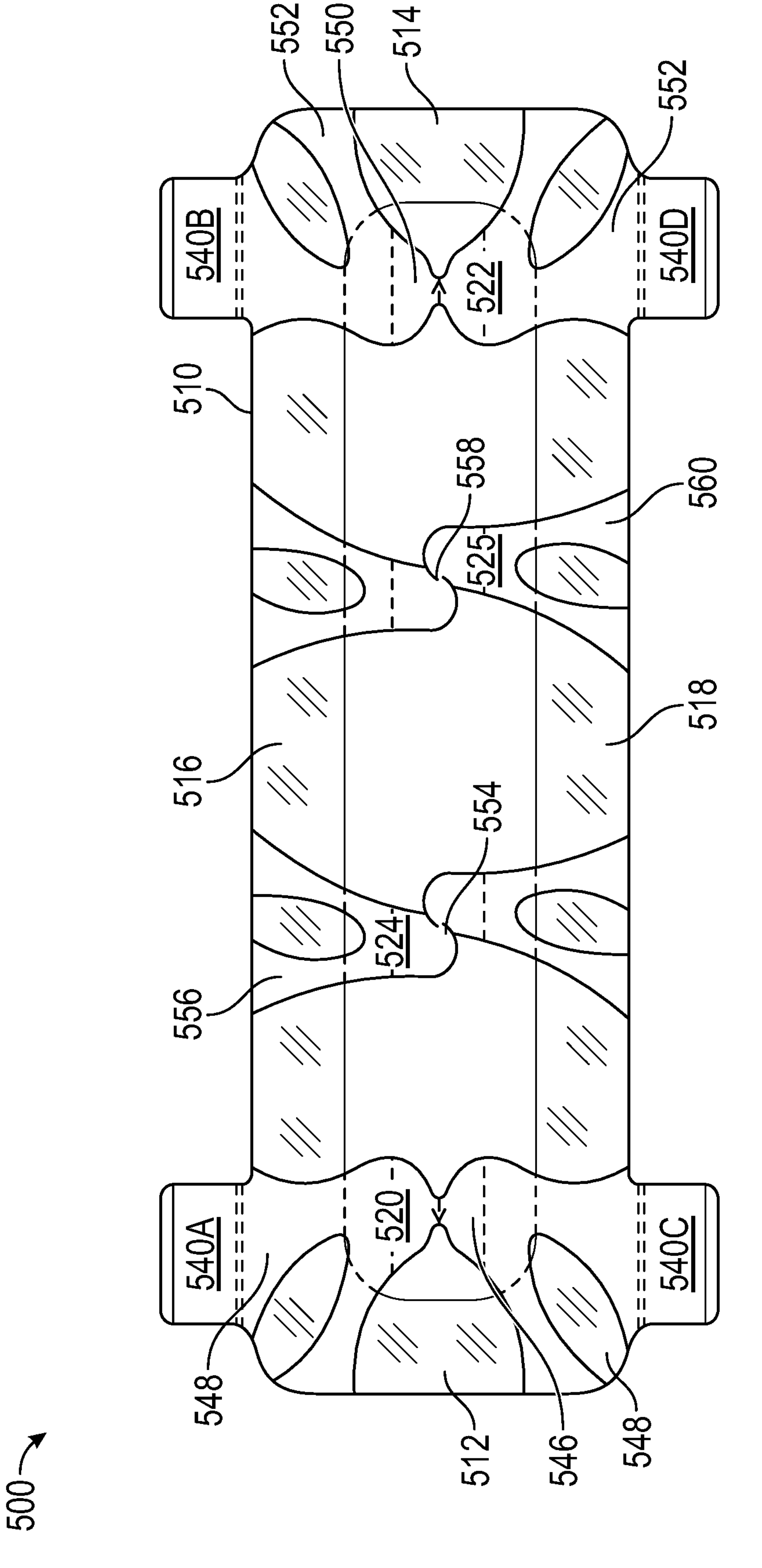
FIG. 5 is a schematic top plan view of one embodiment of a wound dressing.

FIG. 5 illustrates a wound dressing 500. Wound dressing 500 includes all numbered features of wound dressing 200, including those numbered accordingly. Wound dressing 500 further illustrates first support network 520 including a first hub 546. First hub 546 includes phalange(s) 548 extending from first hub 546 to perimeter 510. As shown, phalange(s) 548 extend to first edge 516, second edge 518, first end 512, and second end 514. Second support network 522 includes a second hub 550. Second hub 550 includes phalange(s) 552 extending from second hub 550 to perimeter 510. As shown, phalange(s) 552 extend to first edge 516, second edge 518, first end 512, and second end 514. Third support network 524 includes a third hub 554. Third hub 554 includes phalange(s) 556 extending from third hub 554 to perimeter 510. Fourth support network 525 includes a fourth hub 558. Fourth hub 558 includes phalange(s) 560 extending to perimeter 510. Wound dressing 500 further includes edge handling tabs 540A, 540B, 540C, and 540D.

Figure 6:
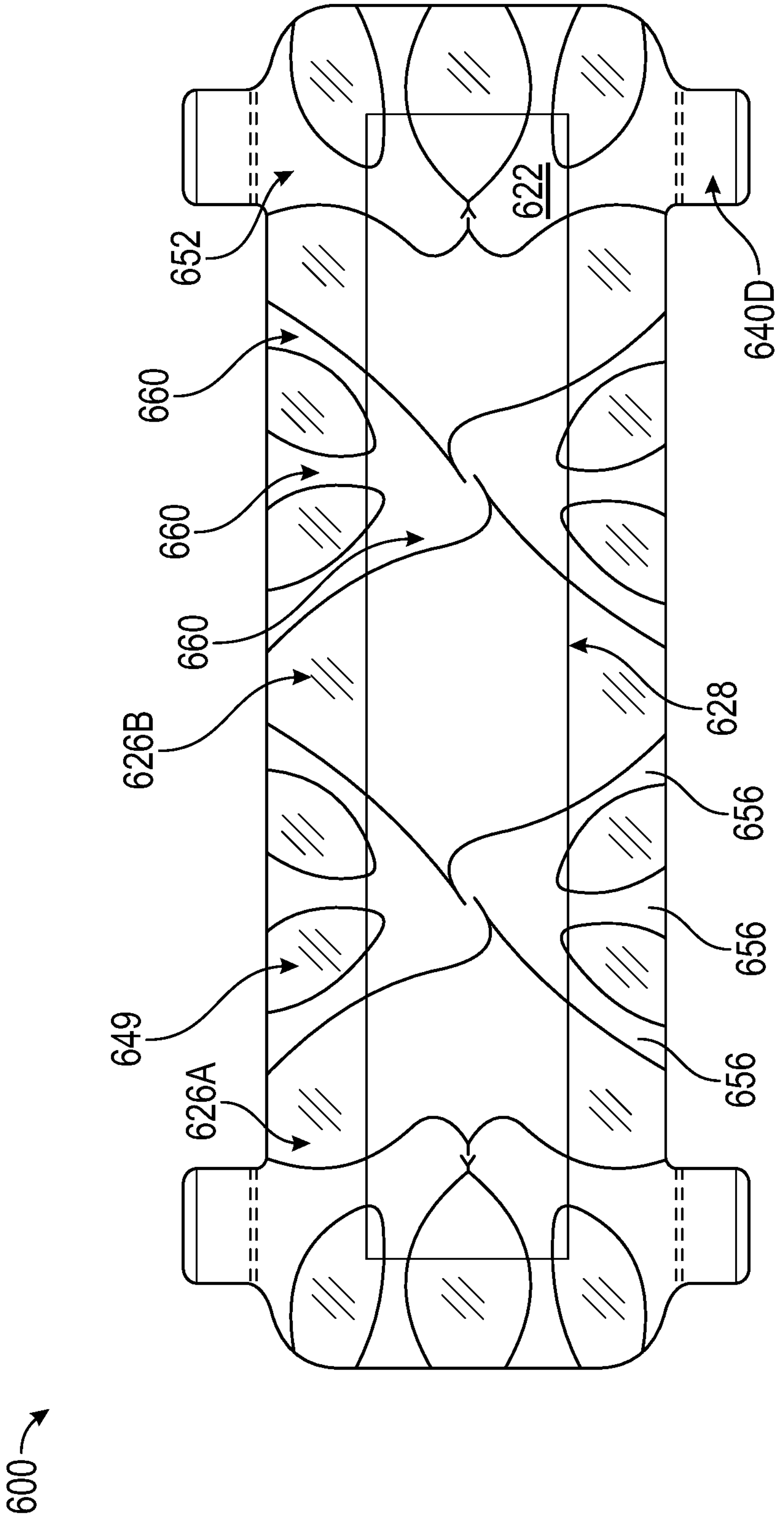
FIG. 6 is a schematic top plan view of one embodiment of a wound dressing.

FIG. 6 illustrates a wound dressing 600. Wound dressing 600 includes all numbered features of wound dressings 200 and 500, including those numbered accordingly. Wound dressing 600 differs from wound dressing 500 in that it includes additional phalange(s) 656 and 660. Also shown here is phalange 652 of second network 622, handling tab 640D, exposed surfaces 626A and 626B, and exposed phalange surface(s) 649 which separate phalanges exposing the second surface of the flexible substrate.

Figure 7:
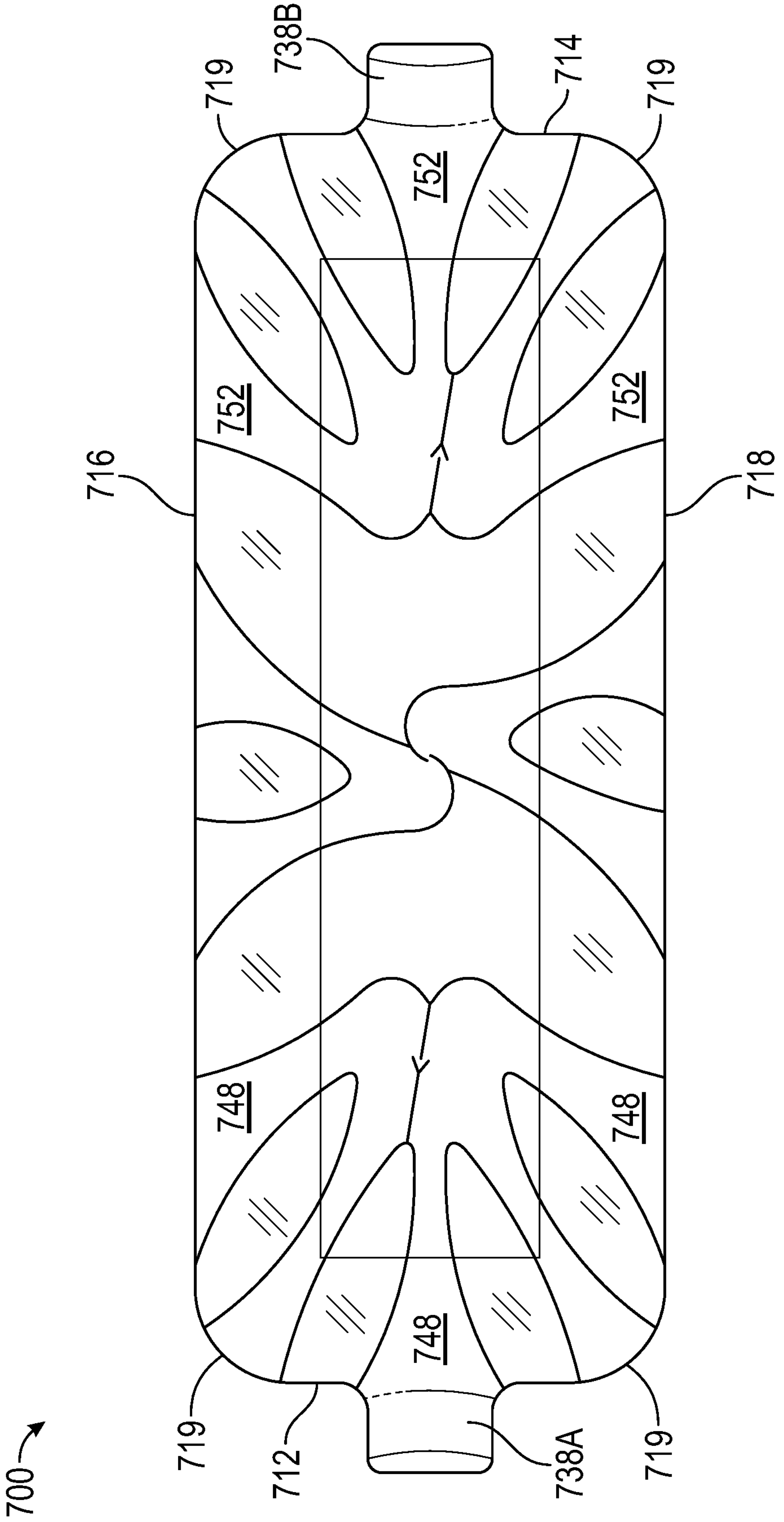
FIG. 7 is a schematic top plan view of one embodiment of a wound dressing.

FIG. 7 illustrates a wound dressing 700. Wound dressing 700 includes all numbered features of wound dressings 100, 300, and 400, including those numbered accordingly. Wound dressing 700 differs from wound dressing 400 in that it includes additional phalange(s) 748 and 752, wherein phalanges 748 and 752 extend to first end 712, second end 714, first edge 716, second edge 718, and corner(s) 719. Wound dressing 700 further differs from wound dressing 400 in that in includes end handling tabs 738A and 738B instead of edge handling tabs.

Figure 8:
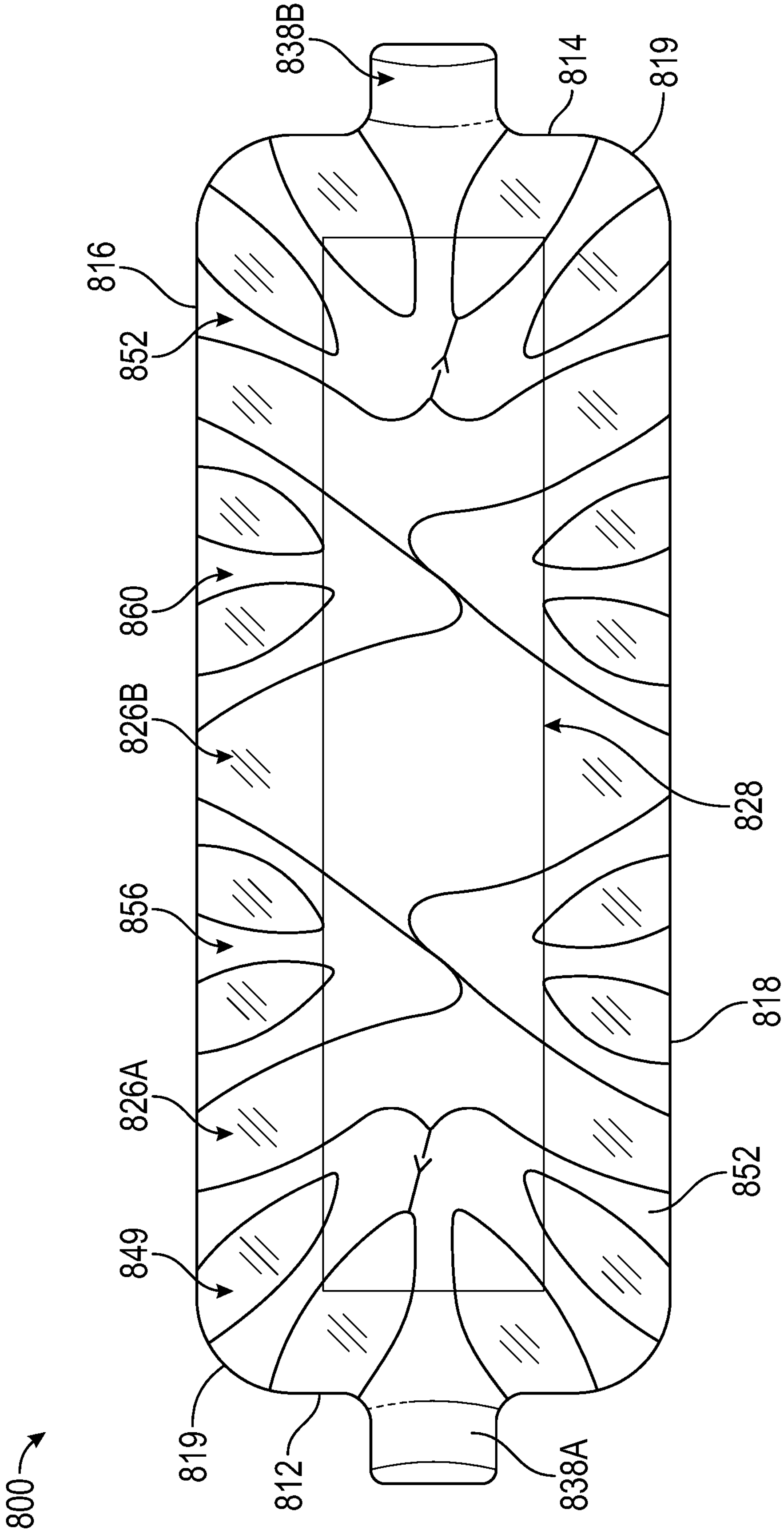
FIG. 8 is a schematic top plan view of one embodiment of a wound dressing.

FIG. 8 illustrates a wound dressing 800. Wound dressing 800 includes all numbered features of wound dressings 200, 500, and 600, including those numbered accordingly. Wound dressing 800 differs from wound dressing 600 in that it includes addition phalanges 848 and 852, wherein phalanges 848 and 852 extend to first end 812, second end 814, first edge 816, second edge 818, and corner(s) 819. Wound dressing 800 further differs from wound dressing 600 in that in includes end handling tabs 838A and 838B instead of edge handling tabs.

Figure 9:
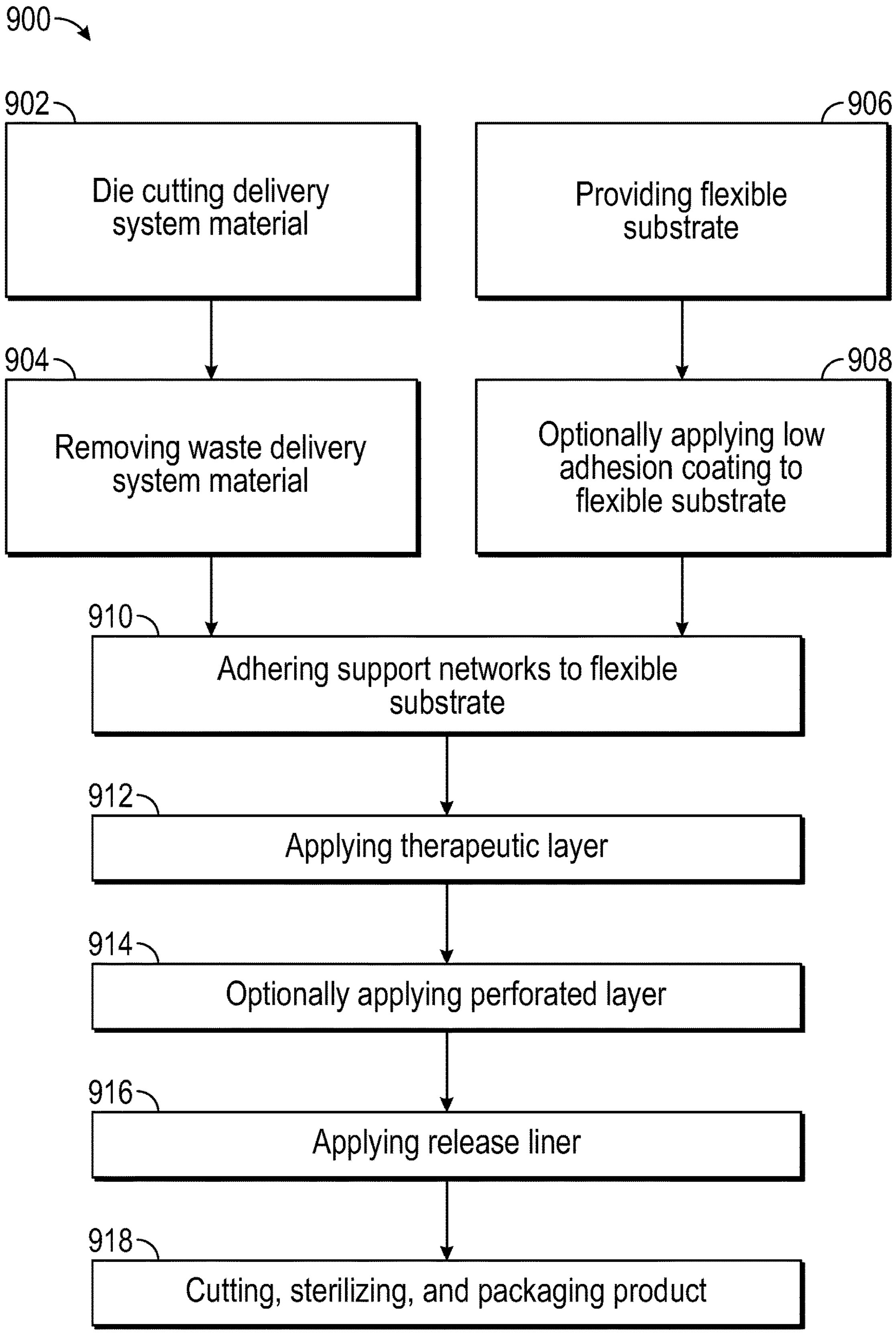
FIG. 9 is a flow chart of a method of manufacturing the wound dressings of the present disclosure.

FIG. 9 outlines a method 900 for the manufacturing of a wound dressing(s) described herein. A delivery system material is die cut 902 according to a predetermine pattern to provide delivery system support networks. Waste delivery system material is removed from the delivery system support networks 904. A flexible substrate is provided 906. A low adhesion coating is optionally applied 908 to a second surface of the flexible substrate. The delivery system support networks are further adhered 910 to the flexible substrate. A therapeutic layer is applied 912 to the first surface of the flexible substrate. An optional perforated layer is applied 914 over the therapeutic layer, and a release liner is applied 916 over the perforated layer. The product is cut, sterilized, and packaged 918.

Figure 10:
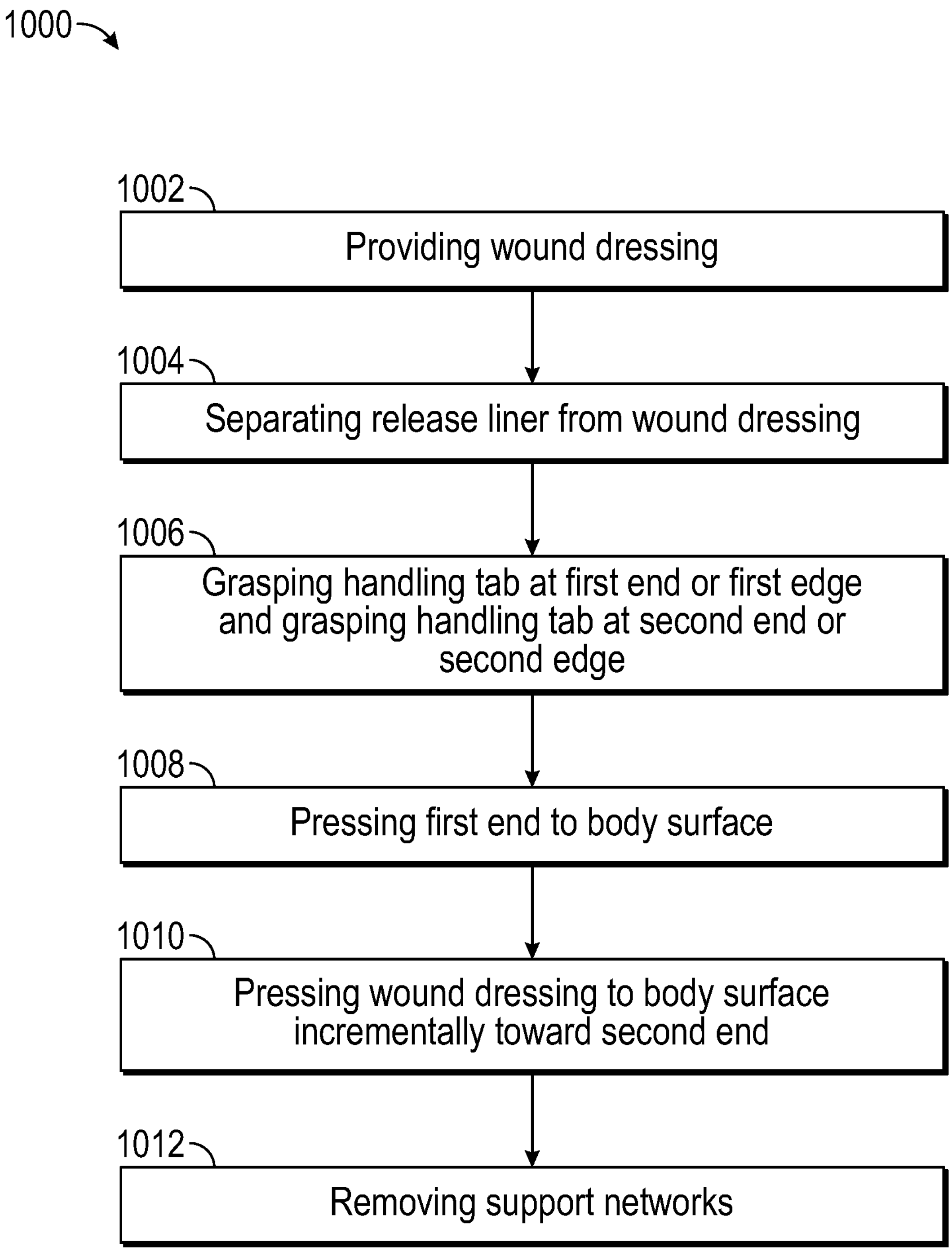
FIG. 10 is a flow chart of a method of using the wound dressings of the present disclosure.

FIG. 10 outlines a method 1000 for using a wound dressing(s) described herein. The method includes providing the wound dressing 1002. The release liner is separated from the dressing 1004. A user(s) grasps a handling tab at the first end or first edge and grasps a handling tab at the second end or second edge 1006. The first end of the wound dressing is pressed to a body surface and the wound dressing is further pressed to the body surface incrementally toward the second end until the application is complete 1008. The support network is removed from the dressing 1010.

Elongated Composites

In many embodiments, the elongated composite may include a flexible substrate including a first surface and a second surface opposite the first surface; a perimeter including a first end, a second end opposite the first end, a first edge and a second edge opposite the first edge; a length defined by a distance between the first end and the second end; and a width defined by a distance between the first edge and the second edge.

In some embodiments, the elongated composite may include a therapeutic layer. The therapeutic layer may contact the first surface of the flexible substrate.

In some embodiments, the elongated composite may include a perforated layer. The perforated layer may contact one or more of the first surface of the flexible substrate and a therapeutic layer.

In some embodiments, the elongated composite may include a release liner. The release liner may contact one or more of the first surface of the flexible substrate, a therapeutic layer, and a perforated layer.

Dimensions

In some embodiments, the elongated composite may include a length value of between about 200 mm to about 380 mm. For example, the length may be a value in mm of about 200, 210, 220, 230, 240, 250, 260, 270, 280, 290, 300, 310, 320, 330, 340, 350, 351, 352, 353, 354, 355, 356, 357, 358, 359, or 360, or a value between a range of any of the preceding values. For example, the length may be between about 352 mm and about 353 mm, e.g., 352.5 mm; between about 351 mm and about 353 mm, between about 350 mm to about 360, or the like.

In some embodiments, the elongated composite may include a width of about 85 mm to about 115 mm. For example, the width may be a value in mm of about 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, or 115, or a value between a range of any of the preceding values. For example, the width may be between about 100 mm and 115 mm, between about 102 mm to about 114 mm, or the like.

In some embodiments, the elongated composite may include a length to width ratio of about 2:1 to about 4.5:1. For example, the ratio may be a value of about 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, or 4:5:1, or a value between a range of any of the preceding values, for example, between about 3:1 to about 4:1, or the like.

In some embodiments, the dimensions of the elongated composite are equal to dimensions of the flexible substrate. The flexible substrate dimensions may be any of the preceding values or within any preceding ranges of values.

Flexible Substrate

In many embodiments, the flexible substrate may be conformable and resilient. For example, the flexible substrate may conform to nonplanar anatomical surfaces, e.g., knees, elbows, or the like. The flexible substrate may be capable of stretching to accommodate movement of a joint or spine, while providing enough resilience to maintain conformability when the joint is returned to an unflexed position. In some embodiments, the flexible substrate has an ultimate elongation of greater than 200%. In other embodiments, the flexible substrate has an ultimate elongation of greater than 400%. Further, for example, the flexible substrate may allow for guided curvature in order to adequately cover nonlinear wounds with a linear wound dressing.

Suitable materials for flexible substrates include, for example, nonwoven fibrous webs, woven fibrous webs, knits, and films. In many embodiments, flexible substrates of the present disclosure include elastomeric polyurethane, co-polyester, and/or polyether block amide films. These films combine the desirable properties of conformability, high moisture vapor permeability, and transparency desired in certain flexible substrates. Exemplary flexible substrate materials may include thin moisture vapor permeable films made from polyurethane resins such as ESTANE 58237 and ESTANE 58309 (Lubrizol, Brecksville, OH) or ELASTOLLAN 1170A or 1185A (BASF, Ludwigshafen, Germany). In some embodiments, the films may have a thickness between about 15 and about 35 microns. The film thickness may be in microns about 15, 20, 25, 30, or 35, or within a range between any of the preceding values, for example, between about 20 and about 25, or the like.

In some embodiments, the flexible substrate may be made up of a single layer. In other embodiments, the flexible substrate may include more than one layer of one or more materials. The flexible substrate is preferably impermeable to liquids but permeable to moisture vapor. In some embodiments, the flexible substrate is translucent or transparent (e.g., transparent polymeric elastic film). Other layers that may be combined with a thin polyurethane film include, for example, elastic non-wovens made from blends of KRATON G1643 (Kraton Corporation. Houston, Texas) and polypropylene, polyester, or nylon.

In various embodiments, the flexible substrate may be coated with a pressure-sensitive adhesive on the first surface (facing the skin). The pressure-sensitive adhesive may include one or more of an acrylate copolymer, a rubber-based polymer (e.g., tackified natural rubbers, synthetic rubbers, and styrene block copolymers), a polyurethane polymer, and a silicone-based polymer. In some embodiments, an acrylic adhesive may include a copolymer of at least one C4-C12 alkyl (meth)acrylate such as isooctyl acrylate or 2-ethylhexylacrylate and at least one high Tg (e.g. polar) co-monomer such as (meth)acrylamide. N-vinyl pyrrolidone, poly(ethylene oxide) acrylate, or a mixture thereof. In some embodiments, an acrylic adhesive may include at least 90 wt.-% C4-C12 alkyl (meth)acrylate(s). Suitable examples include a 90:10 isooctyl acrylate to acrylic acid copolymer, a 70:15:15 isooctyl acrylate to ethylene oxide acrylate to acrylic acid terpolymer, and/or a 25:69:6 2-ethylhexylacrylate to butyl acrylate to acrylic acid terpolymer. Another example acrylic adhesive may include a 65:15:20 2-ethylhexylacrylate to acrylic acid to copolymer (97:3 isooctyl acrylate to acrylamide copolymer) blended with a nonreactive polyalkylene oxide copolymer, such as the adhesive under the trade designation PLURONIC® (BASF Corporation; Ludwigshafen. Germany).

In some embodiments, the flexible substrate may be coated with a low adhesion coating on the second surface. The low adhesion coating may serve to minimize friction and reduce adhesion of tapes or other securing devices. For example, the low adhesion coating may reduce the number of dressing changes caused by undesired dressing removal when tapes or other securing devices are removed. Further, the low adhesion coating may limit friction between the dressing on linens or other fabrics, thereby offering additional protection from accidental removal. In some aspects, the low adhesion coating may facilitate bonding of the delivery system to the flexible substrate. The low adhesion coating may cover at least a portion of the second surface. Suitable low adhesion coatings can be found, for example, in U.S. Pat. No. 5,531,855.

In some embodiments, the pressure-sensitive adhesives may be silicone-based. Silicone-based adhesives effectively secure dressings to skin and produce little or no skin damage upon removal. Examples of a suitable pressure sensitive silicone gel adhesive are radiation cured silicone oils or gums that include silicate tackifier resins. Generally, the silicone oils or gums may include polydiorganosiloxanes. i.e., materials comprising a polysiloxane backbone. In some embodiments, the nonfunctionalized silicone materials can be a linear material comprising a siloxane backbone with aliphatic and/or aromatic substituents. In some embodiments, the nonfunctionalized polydiorganosiloxane materials may include branched substituents. Suitable silicate tackifying resins include those include MQ silicate tackifying resins. MQD silicate tackifying resins, and MQT silicate tackifying resins. These silicate tackifying resins usually have a number average molecular weight in the range of 100 to 50,000 g/mol, e.g., 500 to 15,000 g/mol. Suitable silicate tackifying resins are commercially available from sources such as Dow Corning (Midland. MI) (e.g., DC2-7066). Momentive Performance Materials (Waterford. NY) (e.g., SR545 and SR1000), and Wacker Chemie AG (Munich, Germany) (e.g., BELSIL TMS-803).

Other examples of silicone adhesives may include products marketed with the trade names: Dow Corning MG 7-9850 (Dow Corning. Midland. MI). Wacker SILPURAN® 2110 and 2130 (Wacker Chemie AG. Munich, Germany). Bluestar SILBIONE® RT Gel 4317 and 4320 (Bluestar Silicone USA Corp. East Brunswick, NJ). Nusil MED-6345 and 6350 (Nusil Technology LLC. Carpinteria. CA).

For skin-contact adhesives, it is desirable for the adhesive to transmit moisture vapor at a rate greater to or equal to that of human skin. While such characteristics can be achieved through selection of appropriate adhesives, it is also contemplated that other methods of achieving a high relative rate of moisture vapor transmission may be used, such as perforating the adhesive or pattern-coating the adhesive. Each of the securing or skin-contact adhesives can optionally be applied in a discontinuous manner.

Inclusion of medicaments or antimicrobial agents in the adhesive is also contemplated. Examples of suitable medicaments include chlorhexidine gluconate and silver-based compounds, such as silver oxide, silver chloride, and silver sulfate.

Therapeutic Layer

In various embodiments, the elongated composite may further include a therapeutic layer.

In several embodiments, the therapeutic layer extends between and underneath at least a portion of the each of the hubs of the various support networks to act as a bridge or stiffening agent between the support networks. This added stiffening reduces the chances that the flexible substrate will fold onto itself during application of the dressing to a wound site.

In some embodiments, the therapeutic layer may have the same general shape as the elongated composite and/or flexible substrate.

In some embodiments, the therapeutic layer may be removed from the perimeter of the elongated composite and/or flexible substrate. In some embodiments, the therapeutic layer may have the same general shape as the elongated composite and/or flexible substrate. In many embodiments, the therapeutic layer may have a perimeter value less than the perimeter value of the elongated composite, resulting in an island-type dressing. The perimeter of the therapeutic layer may be less than 90, 85, 80, 75, 70, 65, 60, 55, or 50 percent of the elongated composite perimeter, or a value between a range of any of the preceding values. In some embodiments, the perimeter of the therapeutic layer is less than 50 percent of the elongated composite perimeter.

In many embodiments, the therapeutic layer is removed from the first end and the second end by an end distance. This may allow a user may cut away one or more end distance(s) in order to apply consecutive wound dressings to cover exceptionally long wounds or traumas with uninterrupted therapeutic layers. Each end distance may independently be about 15 to about 35 mm. For example, each end distance may independently be in mm of about 15, 20, 25, 30, or 35, or within range of any of the preceding values, for example, between about 20 and about 30, between about 20 and 25, or the like.

In many embodiments, the therapeutic layer is removed from the first edge and the second edge by an edge distance. Each edge distance may independently be about 15 to about 35 mm. For example, each edge distance may independently be in mm of about 15, 20, 25, 30, or 35, or within range of any of the preceding values, for example, between about 20 and about 30, between about 20 and 25, or the like.

In several embodiments, the therapeutic layer may include one or more areas wherein the material is interrupted, e.g., by partial or full cuts, perforations, fenestrations, gaps, thinner material, or the like. Such areas may provide additional flexibility and allow for the wound dressing to better maneuver along nonlinear surfaces upon application of the wound dressing. In some embodiments, the interruptions may be approximately parallel with the ends of the therapeutic layer. In other embodiments, the interruptions may be at an angle of less than 45 degrees relative to the orientation of the end of the therapeutic layer. In many embodiments, the interruptions do not extend from one edge to the other edge of the therapeutic layer.

In various embodiments, the therapeutic layer may include an absorbent pad. The absorbent pad may include one or more layers, and each layer may include one or more absorbent materials. In some embodiments, the absorbent pad is flexible.

In some embodiments, the absorbent pad may be translucent or transparent, thus allowing for visual inspection of the wound without removal of the wound dressing.

In many embodiments, the absorbent pad may include synthetic or natural materials, including woven or nonwoven materials (e.g., woven or nonwoven cotton or rayon), hydrocolloids (e.g., pectin, gelatin, carboxymethylcellulose (CMC), cross-linked carboxymethylcellulose (X-link CMC), cross-linked polyacrylic acid (PAA)), polymer gels (e.g., hydrogels), foams, collagens, hydrofibers, alginates, and combinations thereof. In some embodiments, the absorbent pad may include a polymeric fabric, a polymeric foam, and combinations thereof. For example, the polymeric fabric may be a nonwoven and the polymeric foam may be the foam used in the TEGADERM foam adhesive dressing available from 3M Company, St. Paul, Minn. In certain embodiments, the polymeric foam is a polyurethane foam.

In certain embodiments, the absorbent pad may include an absorbent hydrogel. The absorbent hydrogel may include a swellable, crosslinked poly(N-vinyl lactam), such as crosslinked polyvinylpyrrolidone, a swelling agent such as polyglycerol-3, and an optional modifying polymer such as hydroxypropyl guar present in an amount sufficient to form a cohesive, absorbent hydrogel composition. The swellable poly(N-vinyl lactam) may be present in an amount from about 10 to about 50 wt % of the composition. When the poly(N-vinyl lactam) is poly(N-vinyl pyrrolidone), poly(N-vinyl pyrrolidone) may be present in an amount from about 15 to about 45 wt % of the composition. In some embodiments, the poly(N-vinyl pyrrolidone) may be present in an amount from about 18 to about 35 wt % of the composition. In some embodiments, the amount of swelling agent may be present in an amount from about 50 to about 90 wt % of the composition. In some embodiments, the optional modifying polymer may be present in an amount of about less than 5 wt % of the composition.

In many embodiments, the absorbent hydrogel may include less than 25 wt % water with respect to the composition.

In many embodiments, the absorbent pad may include one or more active agents. For example, the absorbent pad may include growth factors (e.g., TGF, FGF, PDGF, EGF, or the like), antibacterial agents (e.g., penicillin, neomycin sulfate, sulfonamides, sulfadiazine, silver sulfadiazine, trimethoprim, povidone iodine, iodine, silver, silver chloride, chlorhexidine (e.g., chlorhexidine gluconate), or the like), antifungal agents (e.g., griseofulvin, chlormidazole hydrochloride, clotrimazole, ketoconazole, miconazole, miconazole nitrate, nistatin, tolnaftate, or the like), disinfectants and antiseptics (e.g., benzalkonium chloride, cetalkonium chloride, chlorhexidine gluconate, ethanol, iodine, methylbenzethonium, povidone iodine, isopropanol, silver, silver oxide, silver salts such as silver lactate and silver chloride, triclosan, or the like), local anesthetics (e.g., tetracaine, benzocaine, prilocaine, procaine, or the like), debriding agents, anti-inflammatory agents (e.g., indomethacin, ketoprofen, dichlofenac, ibuprofen, or the like), astringents, enzymes, nutrients (e.g., vitamins. minerals, oxygen, or the like), drugs for cataplasms (e.g., menthol, camphor, peppermint, capsicum extract, capsaicin, or the like), and odor absorbing agents (e.g., zeolites, silicates, chitosans, cyclodextrins, or the like).

In many embodiments, the absorbent pad may include chlorhexidine gluconate.

Perforated Layer

In some embodiments, the elongated composite may include a perforated layer.

In some embodiment, the perforated layer may be in at least partial contact with the first surface of the flexible substrate. The perforated layer may be in at least partial contact with the therapeutic layer.

In some embodiments, the perforated layer may be liquid permeable. In some embodiments, the perforated layer may be applied discontinuously (e.g., pattern coated, perforated or slit) such that liquid or wound exudate can pass through the perforate layer and reach the therapeutic layer. In some embodiments, the perforated layer is at least 5% open, i.e., at least 5% perforated. In other embodiments, the perforated layer is at least 15% open.

In some embodiments the perforated layer is coextensive with the elongated composite. In some embodiments, the perforated layer is coextensive with the therapeutic layer.

The perforated layer is preferably soft, flexible, conformable, non-irritating and non-sensitizing. The perforated layer is preferably transparent to allow for visual inspection of the wound site.

In some embodiments, the perforated layer may include an adhesive on one or more surfaces of a perforated layer. The adhesive may facilitate bonding of the perforate layer to one or more of the flexible substrate, therapeutic layer, and/or wound site. The adhesive may include any adhesive described herein. The perforated layer may be a porous adhesive layer. The adhesive may include any adhesive described herein. In some embodiments, the perforated layer may prevent adhesion to the wound.

In some embodiments, the perforated layer may include a moisture vapor permeable film, perforated film, porous film, woven, non-woven or knit webs, or scrims. The perforated layer may include polyurethane, polyethylene, polypropylene, polyamide or polyester materials. For example, the perforated layer may include polyurethane films such as those available under the trade designation ESTANE (Lubrizol in Brecksville. Ohio); elastomeric polyesters such as those available under the trade designation HYTREL (E.I. duPont deNemours & Co., Wilmington. Del.); and/or polyether block amides such as those available under the trade designation PEBAX (Elf Altochem North America. Philadelphia, Pa). Other useful films include those made from polyurethane resins under the trade designation ELASTOLLAN (BASF. Ludwigshafen. Germany).

In some embodiments, the perforated layer may be between about 15 microns and about 200 microns thick. In some embodiments, the perforated layer may be between about 15 and about 35 microns thick. In some embodiments, the perforated layer may have an ultimate elongation of at least 200%. In other embodiments, the perforated layer may have an ultimate elongation of at least 400%.

Release Liner

In several embodiments, the elongated composite may further include a release liner. The release liner may be releasably attached to one or more of the flexible substrate, therapeutic layer, and perforated layer. The release liner is removed to expose a wound contact surface prior to application of the wound dressing.

Release liners may include kraft papers, polyolefin, polyethylene, polypropylene, polyester or composites of any of these materials. In some embodiments, the release liners may be coated with one or more release agents, e.g., fluorochemicals or silicones. The release liner may be any commercially available release liner such POLYSLIK™ silicone release papers available from Loparex (Cary. North Carolina); Silicone 1750 coated films from Infiana (Forchheim, Germany), and 3M Scotchpak™ 9741 Release liner from 3M Company (St. Paul, Minnesota).

Delivery Systems

In various embodiments, the wound dressings of the present disclosure include a delivery system. The delivery system may include a plurality of support networks capable of assisting a user to deliver the wound dressing to a subject. The support networks allow for coverage of long wounds, especially nonplanar wounds that require dressing conformability and resiliency. The delivery system provides stability of the wound dressing for proper application yet enables high conformability and resiliency of the dressing. Without delivery systems, such wound dressings would fold onto themselves, wrinkle, and/or otherwise fail to adequately cover the wound.

Support Networks

In various embodiments, the delivery system includes a first support network, a second support network, and a third support network.

In some embodiments, the delivery system may further include a fourth support network.

The number of support networks for adequate stability depends upon, for example, the dimensions of the wound dressing and the degree of flexibility in the elongated composite. Longer wound dressings tend to require more support networks.

In some embodiments, the delivery system may include more than four support networks.

In several embodiments, the support networks may be separated from each other by exposing the flexible substrate surface. The distance between any two adjacent support networks, e.g., first and third, third and second, third and fourth, fourth and second, may be between about 10 mm and about 100 mm. In some embodiments the distance between any two adjacent support networks may be in mm about 10, 15, 20, 25, 30, 35, 40, 45, 50, 55, 60, 65, 70, 75, 80, 85, 90, 95 or 100, or within a range between any of the preceding values, e.g., between about 40 mm and about 60 mm, between about 20 mm and about 50 mm, or the like. In some embodiments, the distance between any adjacent support network is no greater than about 150 mm. In many embodiments, the distances between adjacent support networks may be the same or different. Any combination of distances between adjacent support networks cannot exceed the length of the elongated composite described herein.

In many embodiments, each support networks may include a hub, e.g., a first, second, third, and fourth hub, respectively. Each hub may be medially nested along the width of the elongated composite.

In some embodiments, one or more hubs are perforated, have cuts, or lines of weakness to allow for removal of a portion of the support network independent of the entire support network.

In many embodiments, each hub may include at least one phalange extending from the hub to the perimeter of the elongated composite and/or flexible substrate. The at least one phalange may extend to the first end, the second end, the first edge, the second edge, or any corner thereof. Exceptional stability is noted with phalanges extending to or near corners.

In several embodiments, a hub may include a plurality of phalanges. The number of phalanges may be the same or different for each respective hub. In some embodiments, a hub may include 1 to 8 phalanges, e.g., 1, 2, 3, 4, 5, 6, 7, or 8, or a value or range between any of the preceding values, e.g., between 2 and 6, or the like. For example, a first hub may include 4 phalanges and a third hub may include 6 phalanges, or the like.

In several embodiments, one or more phalanges of the first and/or second support network may extend to the first and second ends, respectively.

In several embodiments, one or more phalanges of the first and/or second support networks may extend to the first and second edges, respectively.

In several embodiments, one or more phalanges of the first and second support networks may extend to a corner.

In several embodiments, the first and/or second support networks may include one or more phalanges extending to one or more of the respective ends, edges, and corners.

In many embodiments, one or more of the first support network and the second support network may include at least one phalange extending beyond the perimeter to form a handling tab. The at least one phalange may extend past the first end, second, end, first edge, second edge, corners. In some embodiments, the first end and second ends may include at least one handling tab each. In some embodiments, the first edge and second edge may include at least one handling tab. In some embodiments, the first edge and second edge may include two handling tabs each. In some embodiments, the first end and second end may each include a handling tab, and the first edge and second edge may each include at least one handling tab.

In some embodiments, a straight line passing from one or more handling tabs to the opposite side traverses the therapeutic layer. For example, first support network handling tabs at the first edge and/or second edge may be positioned such that at least one line passing through any part of the tab(s) traverses the therapeutic layer.

In several embodiments, the third and/or fourth support networks may include one or more phalanges extending to the first and second edges.

In many embodiments, the plurality of phalanges of a give support network may be separated by exposed surface of the flexible substrate.

In some embodiments, a phalange may have a nonuniform width extending from a hub to the perimeter. For example, a phalange may be narrower proximal to the hub and wider distal to the hub. In other embodiments, a phalange may have a uniform width extending from a hub to the perimeter. In some embodiments, phalanges of a delivery system may include only uniform widths, only nonuniform widths, or both uniform and nonuniform widths.

In some embodiments, any given support network may be symmetrical, e.g., with respect to one or more of hub shape and phalange shape and count. In other embodiments, any given support network may be unsymmetrical.

In some embodiments, some support networks may be symmetrical with other support networks, e.g., first and second support networks, or third and fourth support networks, may be symmetrical with each other. In other embodiments, some support networks may be unsymmetrical with other support networks.

In many embodiments, the support networks are made from a material more rigid than that of the flexible substrate to prevent the flexible substrate from wrinkling and/or folding during application.

In some embodiments, the support networks may include one or more materials selected from polyethylene/vinyl acetate copolymer, polyvinylacetate-coated paper, polyester film, and polyethylene film. The support networks may further include materials such as nonwovens, polymer films, and papers. One example of a support network material includes a polyethylene/vinyl acetate copolymer coated super calendared Kraft paper available from Loparex (Cary. N.C.). Other examples of suitable support network materials include polyethylene/vinyl acetate copolymer coated polyester film, polyvinylacetate coated polyester film, or polyethylene film. In some embodiments, the support networks may further include non-wovens, polymer films, or papers attached to the aforementioned polymer films at distinct locations. One example of a suitable support network material includes the polyester coated film used in the manufacture of the 90024 3M™ TEGADERM™ Hydrocolloid Thin Dressing available from 3M.

In some embodiments, each support network may independently have a thickness between about 15 and about 125 microns.

In some embodiments, one or more support network may independently include a coated polyester film having a thickness of between about 15 and about 55 microns.

In some embodiments, one or more support network may independently include a polyvinylacetate coated polyester film having thickness of between 20 and 125 microns thick.

In some embodiments, a support network may have a uniform thickness. In other embodiments, a support network may have a non-uniform thickness.

In some embodiments, the support networks may be heat-sealable to the flexible substrate with or without a low adhesion coating described herein.

In some embodiments, a bond block material may be located under a portion of each respective hub to prevent bonding of the hub to the second surface of the flexible substrate. This lack of bond at a portion of the hub facilitates removal of the support network after application of the dressing to the trauma site. The bond block material may be paper that is adhered to the underside of a portion of the hub.

Methods of Manufacture

In various embodiments, a method of manufacturing a wound dressing is described. The method may include die cutting a delivery system material to a predetermined pattern to provide a plurality of delivery system support networks. The delivery system material may be any delivery system material described herein. In some embodiments, the die cutting may be afforded using rotary die cutting equipment.

In many embodiments, the method may include removing waste material from the die cutting. The waste removal may involve, for example, the use of a vacuum, air pressure, gravity, and/or small diameter nip rolls.

In many embodiments, the method may include providing a flexible substrate described herein. A low adhesion coating may optionally be applied to a surface of the flexible substrate.

In many embodiments, the method may then include adhering the delivery system support networks to the flexible substrate. For example, the adhering may include heat sealing.

In some embodiments, the method may further include applying a therapeutic layer to the flexible substrate. The therapeutic layer may be any therapeutic layer described herein.

In some embodiments, the method may optionally include applying a perforated layer to one or more of the flexible substrate and therapeutic layer. The perforated layer may be any perforated layer described herein.

In some embodiments, the method may further optionally include applying a release liner to one or more of the flexible substrate, therapeutic layer, and perforated layer. The release liner may be any release liner described herein.

In many embodiments, the resulting wound dressing material may further be cut, e.g., with a rotary die sheeting station, and the individual dressings may be fed into packaging station. Sterilization may occur before or after one or more packaging steps.

In many embodiments, each of the flexible substrate, perforated layer, and release liner may include an adhesive, or an adhesive may be coated thereupon prior to applications.

Methods of Use

In various embodiments, a method for covering a wound is described. The method may include providing a wound dressing described herein. The method may include separating the release liner from the wound dressing. The method may include grasping a handling tab at the first end or first edge and further grasping a handling tab at the second end or second edge. In some embodiments, the grasping may be done by an individual. In other embodiments, the grasping may be done by more than one person. The method may include pressing the first end to a body surface. e.g., skin surface. The wound dressing may be further pressed to the body surface incrementally toward the second end. In some embodiments, the support networks may be removed after application of the wound dressing. In other embodiments, the support networks may be removed after portions of the dressing are applied.

In some embodiments, removal of the support networks may begin with separating the hubs from the elongated composite.

In some embodiments, the body surface may include broken or disrupted skin, e.g., incisions, burns, scrapes, abrasions, infections, rashes, punctures, cuts, skin growths, or the like. The body surface may be nonplanar. The body surface may include a joint. The broken or disrupted skin surface may be linear or nonlinear. In some embodiments, the broken or disrupted skin surface may have a length of between about 125 mm to about 300 mm.

In some embodiments, the incrementally pressing of the wound dressing toward the second end may allow a user to maneuver the wound dressing along non-linear injuries.

In some embodiments, the method may include pressing a portion of the wound dressing to the body surface and removing the support network which supported that portion prior to pressing a further portion of the wound dressing to the body surface.

During application of the wound dressing, the third and/or fourth support networks facilitate maneuvering of dressing to cover a non-linear wound even over a highly contoured body part. For example, the dressing can be applied to the skin and injury between the first and third support networks. Because of the added rigidity of the dressing at the third support network and the highly flexible area of the exposed surfaces between support networks, the dressing can then be maneuvered or angled in a different direction between the third and second (or fourth) support network because of the highly flexible and stretchy nature of the exposed surfaces area between network support networks. This combination of alternating rigidity and flexibility of a dressing may allow one to better cover or treat a non-linear wound or injury.

In some embodiments, the method may further include cutting two or more elongated composites at one or more end distance and applying an additional wound dressing to the skin surface of the subject such that the therapeutic layers of each wound dressing align for uninterrupted coverage of the broken or disrupted skin surface.

Definitions

As used herein, the term "about" is defined as ±10% of a stated value. For example. "about 20" may mean 18 to 22.

As used herein, the term "conformable" describes an object with an ability to adopt the same shape as of another object.

As used herein, the term "hub" is defined as a point of origin or center.

As used herein, the term "nonlinear" is defined as not being straight. With respect to the present disclosure, a nonlinear wound is one that would extend beyond a therapeutic layer when a wound dressing is straightly applied.

As used herein, the term "nonplanar" is defined as not being confined within a single plane. No body part is likely to adhere to the strictest interpretation of such definition. Nonplanar is meant to describe body surfaces that bend out of plane and/or that have a curvature within the dimensions of a given wound dressing.

As used herein, the term "phalange" is defined as an extension from a point of origin.

As used herein, the term "removed" as used in the phrase "removed from the perimeter" means an object, e.g., a therapeutic layer, having dimensions less than said perimeter.

As used herein, the term "resilient" describes an object with an ability to recoil or spring back into shape after bending, stretching, or being compressed.

As used herein, the term "ultimate elongation" means the percentage increase in length that occurs before the object breaks under tension.

As used herein, the term "support network" is defined as an object providing conformational stability to another object. Without support networks, the wound dressings of the present disclosure would collapse upon attempting to apply the wound dressing to a subject.

As used herein, the phrase "a straight line passing from one or more handling tabs to the opposite edge, traverses the therapeutic layer" means that one or more handling tabs is/are positioned such that if one or more end distances were removed from the wound dressing, at least a portion of the handling tabs would remain with the wound dressing since at no point is a user cutting into the therapeutic layer.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A wound dressing comprising an elongated composite and a delivery system, the elongated composite comprising:

a flexible substrate comprising a first surface and a second surface opposite the first surface, a perimeter comprising a first end, a second end opposite the first end, a first edge and a second edge opposite the first edge, a length defined by a distance between the first end and the second end, and a width defined by a distance between the first edge and the second edge; and the delivery system comprising:

a first support network releasably attached to the second surface, the first support network comprising:

a first hub medially nested along the width, and at least one phalange extending from the first hub to the perimeter;

a second support network releasably attached to the second surface, the second support network comprising:

a second hub medially nested along the width, and at least one phalange extending from the second hub to the perimeter; and a third support network releasably attached to the second surface, the third support network comprising:

a third hub medially nested along the width, and at least one phalange extending from the third hub to the perimeter, wherein the third support network is located between the first support network and the second support network;

wherein each of the first support network, second support network, and third support network are disconnected and separated from one another to expose the second surface.

2. The wound dressing of claim 1, further comprising a therapeutic layer adjacent the first surface and removed from the perimeter and extends under at a least a portion of each hub of the support networks.

3. The wound dressing of claim 2, wherein the therapeutic layer comprises an absorbent hydrogel, chlorhexidine gluconate, or a combination thereof.

4. The wound dressing of claim 1, one or more of the first support network and the second support network comprising at least one phalange extending beyond the perimeter to form a handling tab at the first edge and/or second edge.

5. The wound dressing of claim 1, wherein one or more of the first support network and the second support network comprises two to six phalanges.

6. The wound dressing of claim 1, wherein the third support network comprises two to four phalanges.

7. The wound dressing of claim 1, further comprising a fourth support network, the fourth support network comprising: a fourth hub, and one or more phalange extending from the fourth hub to the perimeter, wherein the fourth support network separates the first support network or the second support network from the third support network.

8. The wound dressing of claim 1, wherein a ratio of length to width is between 2:1 to 4.5:1.

9. The wound dressing of claim 1, wherein any exposed second surface between the first support network, the second support network, and the third support network is 10 mm to 100 mm.

10. The wound dressing of claim 1, wherein any exposed second surface is no greater than 150 mm along the length of the elongated composite.

11. A wound dressing comprising an elongated composite and a delivery system, the elongated composite comprising:

a perimeter comprising a first end, a second end opposite the first end, a first edge and a second edge opposite the first edge, a length defined by a distance between the first end and the second end, a width defined by a distance between the first edge and the second edge, a flexible substrate comprising a first surface and a second surface opposite the first surface; and a therapeutic layer adjacent the first surface, wherein the therapeutic layer is removed from the perimeter; and the delivery system comprising:

a first support network releasably attached to the second surface, the first support network comprising:

a first hub, a phalange extending from the first hub beyond the perimeter at the first edge to form a handling tab;

a second support network releasably attached to the second surface, the second support network comprising:

a second hub;

a phalange extending from the second hub beyond the perimeter at the second edge to form a handling tab; and a third support network releasably attached to the second surface, the third support network comprising:

a third hub;

one or more phalange extending from the third hub to the perimeter, wherein the third support network is located between the first support network and the second support network, wherein each of the first support network, second support network, and third support network are disconnected and separated from one another to expose the second surface, and wherein a straight line passing from one or more handling tabs to the opposite edge traverses the therapeutic layer.

12. The wound dressing of claim 11, wherein one or more of the first support network and the second support network comprises two to six phalanges.

13. The wound dressing of claim 11, one or more of the first support network and the second support network comprising at least one phalange extending beyond the perimeter to form the handling tab at the first end and/or the second end.

14. The wound dressing of claim 11, wherein the third support network comprises two to four phalanges.

15. The wound dressing of claim 11, further comprising a fourth support network, the fourth support network comprising: a fourth hub, and one or more phalange extending from the fourth hub to the perimeter, wherein the fourth support network separates the first support network or the second support network from the third support network.

16. The wound dressing of claim 11, wherein a ratio of length to width is between 2:1 to 4.5:1.

17. The wound dressing of claim 11, wherein any exposed second surface between the first support network, the second support network, and the third support network is 10 mm to 100 mm.

18. The wound dressing of claim 11, wherein any exposed second surface is no greater than 150 mm along the length of the elongated composite.

19. The wound dressing of claim 11, wherein the therapeutic layer comprises an absorbent hydrogel.

20. The wound dressing of claim 11, wherein the therapeutic layer comprises chlorhexidine gluconate.

* * * * *